(12) United States Patent
Martynov et al.

(10) Patent No.: US 8,846,064 B2
(45) Date of Patent: Sep. 30, 2014

(54) COSMETIC AND PHARMACEUTICAL COMPOSITIONS HAVING MODIFIED PROTEINS IN THE FORM OF A SUPRAMOLECULAR ASSEMBLY

(76) Inventors: Artur Martynov, Kharkov (UA); Boris S. Farber, Brooklyn, NY (US); Sonya Sophya Farber, New York, NY (US); Aleksandr Sitenko, Khar'kovskaya oblast (UA)

( * ) Notice: Subject to any disclaimer, the term of this patent is extended or adjusted under 35 U.S.C. 154(b) by 338 days.

(21) Appl. No.: 12/931,463

(22) Filed: Feb. 1, 2011

(65) Prior Publication Data
US 2012/0195945 A1    Aug. 2, 2012

Related U.S. Application Data

(63) Continuation of application No. PCT/RU2010/000697, filed on Nov. 22, 2010.

(51) Int. Cl.
*A61K 8/02* (2006.01)
*A61K 9/127* (2006.01)
*A61K 38/54* (2006.01)

(52) U.S. Cl.
USPC .......................... 424/401; 424/450; 424/94.2

(58) Field of Classification Search
USPC ........................................ 424/401, 450, 94.2
See application file for complete search history.

(56) References Cited

U.S. PATENT DOCUMENTS

| 4,446,240 | A | * | 5/1984 | Nerenberg | ..................... | 436/542 |
| 4,708,861 | A | * | 11/1987 | Popescu et al. | ............. | 424/1.21 |
| 5,783,193 | A | * | 7/1998 | Michael et al. | ............ | 424/207.1 |
| 5,986,050 | A | * | 11/1999 | Shalaby et al. | ............... | 530/345 |

* cited by examiner

*Primary Examiner* — Blessing M Fubara
*Assistant Examiner* — Jennifer A Berrios

(57) ABSTRACT

A cosmetic and pharmaceutical formulation for rejuvenation and restoration of the skin, and methods of making this formulation. The cosmetic and pharmaceutical formulations comprise liposomes containing partially acylated proteins with a modification level of 0.1 to 10% of their mass, wherein the proteins are present in the form of a supramolecular assembly.

24 Claims, 1 Drawing Sheet

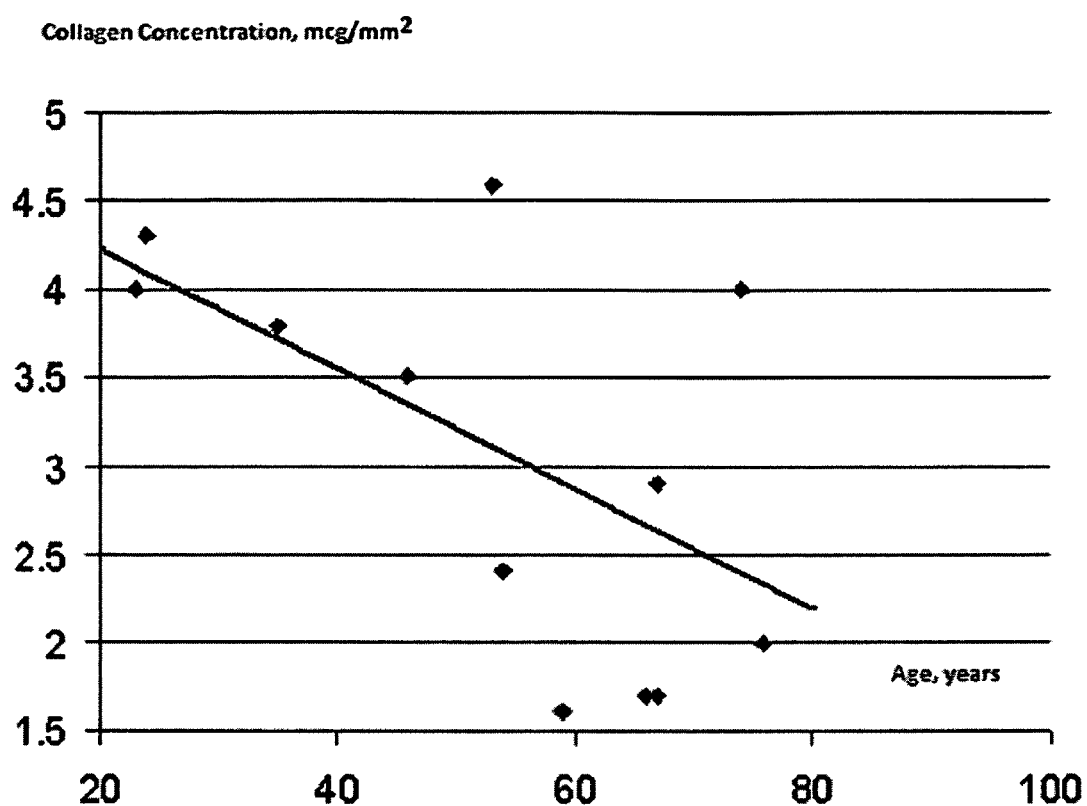

COSMETIC AND PHARMACEUTICAL COMPOSITIONS HAVING MODIFIED PROTEINS IN THE FORM OF A SUPRAMOLECULAR ASSEMBLY

CROSS REFERENCE TO RELATED APPLICATION

This is a continuation of International Application PCT/RU2010/000697 which has an international filing date of Nov. 22, 2010.

SUMMARY OF THE INVENTION

A cosmetological and pharmaceutical formula for rejuvenation and restoring of the skin, including after surgical operations, and the method for obtaining it, containing liposomes with proteins, distinct in that in the capacity of the protein, a system is used based on partially acylated hyaluronidase, insulin, and collagenase in various combinations with a substitution of 0 to 10% of the mass of the protein, where it is used as a gel cream, among other things.

The formula, in the form of a rejuvenating cosmetic cream, may be produced industrially in sufficient quantities, due to the accessibility of all of the formula's components.

TECHNICAL FIELD

This invention is related to pharmacology and cosmetology and may be used in the capacity of a medicinal and cosmetic substance for skin anti-aging, scar reduction, treatment of post-operative peritoneal commissures, increasing the speed of post-operative tissue regeneration, and for the liquidation of cellulite.

Previous Level of Technology

A hypothesis that polypeptide chains of collagen have an increased amount of cross-links in old age has become widespread. The observations lying at the basis of this hypothesis led to the creation of the collagen theory of aging [1]. According to the theory, the accumulation of the number of covalent cross-links in collagen as age increases in an animal brings the proteins to an insoluble state. As a result, it aggregates in the tissues to the detriment of the cells, causing deterioration in the function of the organs and the organism as a whole. Without going into detail with this theory on the level of the body as a whole, we will examine certain details of the construction of collagen fibrils and their transmutation in the skin of animals.

However, it should be noted ahead of time that the reasons for the cross-links in the collagen molecule may be quite varied chemical processes. The formation of transverse cross-links in collagen fibrils is possible due to the modification of the oxylysine remainders of the initial α-chains with the participation of an extracellular enzyme such as lysyl oxidase. The transverse cross-links formed in this manner may be of the lysinonorleucine (—(CH2)4-NH—(CH2)4) or oxy-lysinonorleucine (—(CH2)4-NH—CH2—CHOH—(CH2)2) type. Moreover, cross-links may appear due to creation of S—S bonds between chains with the participation of cysteic remainders that are present in collagen molecules of any type. Therefore, it may be supposed that the relationship between the newly arising bonds of that type and external activity will also be varied. Apparently, the participation of these bonds in the modification of the overall structure of the protein will vary as well.

Collagen fibrils consist of monomers (most likely of fragments); each fragment has three polypeptide chains that are twisted in relation to each other in the form of a spiral. The polypeptide chains have several construction variations: α1(I), α1(II), α1(III), α1(IV) and, analogously, variations on the α2 chains, which are distinct in the order of amino acids and therefore, it seems, their synthesis is coded by different genes. Each α-chain consists of approximately of 1050 amino acids and has a molecular mass of about 100 kDa. The central part of the α-chain consists of about 1000 amino acid fragments connected through an orderly Gly-X-Y sequence. Thus the glycine fragment occupies every third position in the chain. Glycine does not have pendent groups: this is the smallest amino acid (in size). The nitrogen of the amino groups of glycine of one chain is connected with a hydrogen bond to the carbonyl oxygen of the glycine of another chain. There may be more than 600 of these hydrogen bonds created between the three chains that are twisted into a spiral. Regardless of the fact that the energy of these bonds is only 3-5 kcal/mole, the existence of a large number of individual bonds (two bonds on three peptide chains) facilitate the strong maintenance of the three chains in the spiral position.

The remaining two X and Y positions in the abovementioned Gly-X-Y triad can be occupied by other amino acids. Proline and hydroxyproline are often found here. The higher the total-content of proline and hydroxyproline, the higher the stability and melting temperature. Collagen in the skin of a calf contains 232 fragments of these amino acids, and its melting temperature is 39° C., while the collagen in the skin of a codfish contains 155 fragments of proline and hydroxyproline, which leads to a decrease in the melting temperature of the collagen to 16° C. It should also be emphasized that it is not only the total amount of proline and hydroxyproline that determines the stability of collagen, but also the relationship between the indicated amino acids in its molecule. Collagen that contains only proline has a melting temperature of between 20 and 25° C. If hydroxyproline is present instead of proline, the melting temperature rises to 37° C. These changes can be explained by the possibility that the hydroxyproline fragment will create additional hydrogen bonds. Thus the formation of fragments (procollagen) consisting of three peptides twisted into a spiral is cross-linked with other, analogous fragments, forming a collagen fibril.

Collagen fibrils have different constructions depending on their place of localization in the body and on age. For example, the skin of a fetus contains more of the type III collagen than of the type I, while in adults, this ratio changes to the opposite.

Change to the content of the quantity of collagen in the skin in animals during the aging process Returning to the examination of the schedule presented in FIG. 9.6, we note that the total amount of collagen increases in the tail tendons of rats in the aging process. However, this situation contradicts later data [31] and the opinion that is widespread among cosmetology professionals that the total amount of collagen in the skin decreases during the aging process. In the work [2], data is presented in graphic form that indicate that the concentration of collagen in the skin of a human decreases during the aging process.

Without discussing the gigantic range of values in the collagen content in the skin after 50 years of age, the authors come to the conclusion that in order to maintain skin in a normal condition, it is necessary to inhibit the process of the enzymatic degradation of collagen. For this purpose, specific collagenase inhibitors designed to break down collagen fibrils are proposed for use.

However, it would not do to come to rapid-fire conclusions. In the first place, the collagenase enzyme is always found in the location of "its" substratum. It is not important in which organ of the animal the collagen fibrils are found, whether in the tail tendon or in the skin. Collagenase is meant to "unravel" collagen threads, facilitating the process of their renewal, as collagenase, in combination with proteolytic enzymes, destroys the collagen molecule down to low-molecular peptides, which again, as initial material, return to the fibroblasts, in which the synthesis of new collagen precursors takes place. As the authors [2] note, it is due to this process that collagen is constantly renewing itself with a half-cycle (T½) of about 15 days. And now, to resolve the situation presented in the form of a paradox, it must be suggested that for some reason in the process of the body's aging, collagenase in rats slows the breakdown of collagen, moving the dynamic balance toward increasing its synthesis, while human collagenase, conversely, increases its activity, moving the balance toward decreasing the concentration of collagenase. Of course, this situation could be explained by the increase in the speed of collagen synthesis in the skin's fibroblasts. However, a good deal of tangential data allows us to consider this explanation unlikely.

At present, it should be admitted that there is no clarity on the issue of whether collagen collects in the skin during the body's aging process or, conversely, if its concentration decreases. This means that there is a paradox that we have formulated.

To explain the changes taking place in relation to the collagen in human skin, we may use a good deal of data on the influence of enzymes and the peroxide acidization of lipids, which facilitate the creation of cross-linkage, and discuss the possible influence on this process of the changes occurring on a genetic level (see, for example, [2]). However, we could "drown" in the variety of interrelated facts and phenomena without getting to the meat of the (rather complicated) process we are studying. In our view, in situations like these it is useful to use logical constructions that are simplified to a certain degree and which depend on the experimental data at hand, the fairness of which may be verified through experiment.

In this case, we have a process of synthesis and destruction of collagen, taking into account the presence of the dynamic balance between the speed of these reactions (FIG. 1).

Collagen, along with elastin and reticulin, is a strong structure protein localized in the dermis. It makes up the main mass of the dermis (up to 70% of the dry weight) and is a key structural component of connective tissue. This protein, which is specific in its amino acid content and its structure, does not dissolve in water under ordinary conditions (it only swells). Proteolytic enzymes (pepsin, trypsin, papain) only break up the water-soluble fragments of collagen threads. Collagenase is the enzyme that is capable of bringing the collagen thread (fibril) to a soluble state through partial hydrolysis.

Normally, there is a necessary speed equilibrium for these types of processes:
Vsynth=Vdestr.

The speed equilibrium of the synthesis and destruction of collagen determines the presence of a stable dynamic equilibrium. It is natural to suppose that if the speed of the synthesis is increased or the speed of destruction of collagen fragments decreases, a condition of the body may occur connected with the excess collagenization of the dermis and, conversely, if the speed of the synthesis is decreased and the speed of destruction is increased, decollagenization of the tissues of the dermis may occur.

In our opinion, there is an error in thinking that the synthesis of collagen occurs faster than its degradation. In the monograph [3] in the section entitled "The Exchange of Collagen Proteins", the following is stated: "In normal conditions, collagen is synthesized at a speed comparable to the speed of the formation of other proteins. However, collagen disintegrates very slowly (a half-cycle of 50-60), which is a peculiarity of its exchange. The dominance of the synthesis of collagen over its destruction is conditioned on the fact that the newly formed molecules of this protein are too rigid and inaccessible for the activity of proteolytic enzymes." An interesting situation arises. On the one hand, many suppose that the amount of collagen in the skin decreases during the aging process. On the other hand, a decrease in the speed of destruction of collagen while the speed of synthesis remains normal should lead to its buildup.

It seems to us that the author of the above-cited quotation is overly dramatizing the difference in the speeds of the synthesis and destruction of collagen. Visually, at 20 and 30 years of age, and even at an older age, changes in the condition of the skin are fast, affecting only the very "weakest places" of the surface of our bodies (usually the first lines appear in the corners of the eyes, where the thinnest skin is located). Thus the process of the buildup of visible changes to the condition of human skin is drawn out over several decades. If collagen really did break up "very slowly", we would be right to expect that these changes would appear at a much younger age.

Of course, it could have been proposed that for some reason the speed of the degradation of collagen, which is fairly high in the early period of an organism's development, slows down in the following years: for example, due to a decrease in the activity of the collagenase enzyme. Unfortunately, we do not have information on the changes in the activities of collagenase during the process of aging.

Thus the most acceptable variant for describing the condition of the system connected with the synthesis and destruction of collagen threads is that when the body is in a normal state, it has a required speed equilibrium between Vsynth and Vdestr. The size of the absolute values must determine the lifetime of the collagen thread (T). The higher the speed of synthesis and destruction, the lower the value of T, and vice versa.

As has already been noted, in the process of bodily aging, the content of soluble collagen decreases in the skin, while the concentration of its insoluble forms increases, which indicates the increase in the number of intermolecular cross-links and possible changes to the structure of the collagen. All of this could not help but reflect on the process of interaction of collagenase with collagen threads, as enzymes often have significant specificity. Therefore, when cross-links build up in the collagen model, the collagenase, at a given moment, could lose its activity in relation to the collagen substrate that is transformed under the influence of the cross-links. That is, the enzyme could factually lose its ability to "recognize" the collagen molecule and react with it. And actually, it has been found that the cross-linked (insoluble) collagen is resistant to collagenase [4]; in measuring the amount of collagen that does not react to the body's endogenous collagenase, a person's age can be determined.

Thus the body's aging process is accompanied by the buildup of insoluble forms of collagen that do not react with collagenase. This can mean only one thing: a certain quantity of collagen substrate is removed from the equilibrium process of synthesis and destruction of collagen threads mentioned above, and the lifetime (T) of these molecules increases infinitely. As a result, the number of cross-links in the molecules, the collagen, which is not reactive with collagenase, continues to increase, and the collagen matrix of the skin becomes increasingly rigid, which leads to a lowering of the elasticity of the skin and the appearance (fixation) of wrinkles. Rigid collagen builds up in the skin, inevitably facilitating manifestations of its aging. The collagen fragments that have remained unchanged or the fragments whose number of cross-links was not enough to block the destruction of the collagen continue to participate in the cyclic equilibrium process, leading to the synthesis of new, unmodified ("young") collagen structures. In general, this type of cyclical equilibrium process is nothing other than a natural system for the protection of the structure of biopolymers from possible changes, which facilitates the increase in the stability of biological structures and organisms. We will return to these processes that include the participation of other biopolymers. Now we will attempt to formulate the consequences of the participation of collagen structures in the equilibrium process discussed, which is important from cosmetologists' point of view. The total volume concentration of collagen (soluble and insoluble, or collagen not interacting with endogenous collagenase) remains a constant value over the entire lifetime of a human being. This suggestion seems to us to be sufficiently well-founded, since if a mechanism for the regulation of the speed of the synthesis of the peptide precursors of collagen threads in dermal fibroblasts exists, then the basis for this regulation, in our opinion, should be specifically the volume concentration of the skin's collagen matrix. The fact that in the body's aging process a part of the collagen structures are removed from the dynamic equilibrium (synthesis-destruction) being examined may serve as a tangential argument in favor of the existence of a regulation mechanism for the synthesis of collagen precursors in the skin's fibroblasts. Otherwise, we would have inevitably run across the problem of the excess collagenization of the skin's structure. This regulation mechanism is reminiscent of the contact slowing of cell division, in accordance with which in the formation of a monolayer in the process of division, only cells that do not have neighbors are attracted; when the monolayer is fully formed, the division of the majority of types of cells completely ceases!

The suggestion we have given is too serious to not formulate another paradox, which could be called the paradox of the regulation of collagen synthesis.

It is also interesting that the speed of the destruction of collagen in the presence of a mechanism of synthesis regulation, in its turn, may be automatically regulated. Truly, if in the activity zone of endogenous collagenase, cross-linked collagen structures collect, and the quantity of "young" or not very modified collagen threads with which the enzyme may interact gradually decreases, the overall speed of destruction also decreases, dependent on the concentration of the reactive substrate. In addition, the lifespan increases for collagen structures arising in the process of dynamic equilibrium, which, in its turn, increases the likelihood of the aggregation of cross-links and speeds up the aging process. Information exists that indicates that the collagen exchange gradually slows with age, as the development is accompanied by a lessening in the speed of the synthesis and destruction of collagen. It should also be noted that collagenase, when it is not needed, exists in an inactive form (M. Kanungo, 1982). These facts, in our opinion, correspond to the proposal stated above that was formulated in the guise of a paradox. Now we will turn to the possible implications of the proposal stated above. If an aggregate amount of collagen in a unit of skin volume is constant over the course of an entire human life, the necessity of the use of and the beneficial quality of cosmetic preparations containing ingredients of a collagen nature can be called into question. Say we use a cream reparation that contains collagen taken from the connective tissues or cartilage of young animals. It is natural to suppose that the molecules of this kind of collagen have practically no intra- or intermolecular cross-links and are therefore fairly elastic. The obvious result of the application of this cream on the surface of the skin is an instantaneous increase in its elasticity. However, taking into account the skin's permeability limit, it may be supposed that the effect of using this kind of formula will, in the majority of cases, disappear immediately after the cream is removed from the surface of the skin. High-molecular collagen structures cannot penetrate into the depths of the skin to a sufficient degree, remaining on its surface. A completely different situation arises when collagen structures are used that have a molecular mass of less than 100 kDa. With the ability to pass through the transepidermal barrier, these structures, on the one hand, more effectively increase skin elasticity, affecting not only its surface, but also its deeper layers. However, on the other hand, in entering the zone of activity of collagenase, collagen fragments are capable of drawing the enzyme away from interaction with its own skin collagen matrix and, as a result, the speed of the main reaction decreases. A condition arises that is well-known in biochemistry called competitive inhibition of the primary process. This slowing increases the lifespan of its own collagen structures and, accordingly, the likelihood of the creation of intra- and intercellular bonds. All this inevitably leads to an increase in the skin's speed of aging. Thus if our hypotheses are correct, then from the position of the theory of mild cosmetological activities, the use of cream formulas containing collagen fragments capable of passing through the transepidermal barrier can, while apparently demonstrating instant benefit, have negative effects that speed up the process of the aging of the skin's collagen structures.

Thus there is a paradox whose essence is that there may be some doubt of the desirability of the use in cosmetology of any raw sources of collagen origin capable of drawing the collagenase enzyme away from the primary reaction. We propose calling this situation the paradox of diverted bonds, and we will hope that special experiments will confirm or, conversely, allow us to discard the suggestions we have made, which (it should be noted) have some basis in reason.

One more result of the foregoing discussions must be kept in mind. It is connected with the need for the careful checking of the original raw material for the production of cosmetic preparations for compatibility with skin enzymes and, in part, with collagenase.

The collagenase enzyme as an ingredient in cosmetic preparations. There is yet another implication of the function of the dynamic equilibrium process of the synthesis and destruction of collagen fibers that will be of interest to cosmetologists. It is that if the endogenous collagenase located in the collagen matrix zone of the skin begins to "miss" certain collagen structures modified by cross-links that decrease the skin's elasticity when they collect there with age, then the desire arises to help the body through introducing additional quantities of the enzyme. It is necessary that the following major conditions be fulfilled:

the enzyme's molecular mass should facilitate real access to internal skin structures the collagenase introduced must have a lower specificity of activity in comparison with the endogenous collagenase in human skin or interact with a wider selection of substrates interaction with cell systems should be sufficiently attenuated A large number of enzymes exist that have collagenolytic activity.

According to the data of the work [5], a purified collagenase preparation contains a selection of substances with molecular masses from 16 to 32 kDa. The molecular mass of 23.5 kDa dominates (up to 80%). This drug has the ability to break peptide bonds in natural collagen. Depending on the extent of purification, the preparation's collagenolytic activity may be accompanied by trypsin-like, chymotrypsin-like, carbohydrase, and DNAase activities. The present data permits us to suppose that collagenase taken from the livers of king crabs differs in specificity of activity, for example, from preparations of collagenase taken from Clostridium microorganisms. The collagenolytic enzyme from the liver of a crab demonstrates high activity in relation to various types of natural collagen. It, unlike microbial collagenase, breaks apart type III collagen from the skin of a calf and type IV collagen from the ocular lens of a bull. As they are enzymes that are part of the class of cerin proteases, collagenase hydrolyzes specific substrates for trypsin, chymotrypsin, and elastase. It has also been proven [5] that purified collagenase taken from the livers of crabs is compatible with many cell systems in certain concentrations. The processing of the monolayer in test tube cell cultures such as L68, SV1, MDCK, Hep2, and HLCC leads to a rather fast lamination of cells from the solid substrate with the maintenance of their morphology and a low percentage of dead cells at an enzyme concentration of from 0.0001 to 0.01%.

Thus the characteristics of the collagenolytic preparation examined above permitted us to infer the presence of the possibility of its effective use as an addition to cosmetic formulae that prevent or slow the skin aging mechanism connected with the aggregation of cross-links in collagen molecules. Truly, the molecular mass of an enzyme allows it to attain the zone of localization of the collagen threads (the papillary layer of the dermis) with a certain level of likelihood. That rare information on the peculiarities of the specific activity of an enzymatic drug permitted us to hope for the implementation of a unique type of "help" for human endogenous collagenase. For example, to cosmetologists, it is extremely important to involve in the hydrolysis reaction those collagen threads with which a subject's own collagenase can no longer interact. If this process were truly initiated using added exogenic collagenase, that, figuratively speaking, would remind us of the additional janitor effect, cleaning "trash" from corners where the main janitor's brush cannot reach. However, we must admit that we do not have enough grounds for final confirmation of the implementation of this kind of process. As usual in these situations, when there is a lack of information, the paradox of the additional janitor effect can be formulated.

Nevertheless, introduction into a cosmetic substance of collagenase taken from crab livers seems justified from the point of view that in acting on the collagen threads in combination with the endogenous collagenase and thereby speeding up their degradation, the preparation will facilitate a decrease in the life span of collagen threads and, accordingly, a decrease in the likelihood of the aggregation of cross-links. The attenuated activity of the drug on the cell cultures, from the position of the theory of gentle cosmetological activity, permits the movement of the developers of cosmetic substances in the indicated direction. In the work [5], experimental studies were conducted of harmless, biochemical mechanisms of action, and of the "crab collagenase" enzyme complex's effect on the structure of the skin. On the basis of this research, it is recommended that this drug be used in a 0.75% concentration in cosmetic preparations designed for the care of drooping facial skin. Unfortunately, we do not have information on the activity and quality of the collagenases used in these experiments. However, the circumstance that the recommended concentration exceeds the attenuated concentration for cells by a factor of 75-7500 is cause for concern. The reasons for this increase may be connected with distinctions in the activity (purity) of the preparations being tested. However, we find this difficult to believe. Most likely, we are again dealing with cosmetological paradoxes connected with the reckless use of anomalously high concentrations of biologically active ingredients. In this case, the developers of cosmetic substances do not worry what will happen to the cells of the basal layer of the epidermis under the influence of the enzymes in the "recommended" concentrations. If this question were put to a cytologist or a cellular biotechnologist ("culturalist"), curious responses might be received. There is the feeling that cosmetologists are more likely assimilating "the skin business for the masters", since comparable concentrations of the "crab collagen" preparation are used to finish animal hides (information from the Pacific Ocean Institute of Bioorganic Chemistry) to obtain clothing leather, leathers for shoe uppers from raw material from large horned stock and especially elastic leathers made of raw material from swine.

Returning to the main task of cosmetology—that of providing for counteraction of the skin's aging process—and to the theory of mild cosmetological activities that permit influence over biochemical processes and the transmutation of the skin's cell systems, for the implementation of this major task, it must be emphasized that even those enzyme concentrations that were used by the authors of the work [5] to attain their goals (removal of the monolayer from the substrate, division of animal tissues) were apparently unable to serve as an orientation point for the construction of "attenuated" cosmetic substances. The most acceptable concentration of collagenase in cosmetic substances, in our opinion, should not significantly exceed the content of collagenase in the structure of human skin. The cell test systems should restrain the activity of the enzyme for at least a longer period of time than the 5-15 minutes of activity used by the authors of the work [5]. This issue requires detailed examination and possibly experimental verification. We should also not be lulled by the circumstance that the "crab collagen" preparation, which is added to the cosmetic medium at a concentration of 0.75%, positively influences the "morphological structure of the skin". The detailed basis for the concentration would require from the experimental testers the setup of special experiments to discover long-term effects.

It should, however, be noted that in examining this issue, we have consciously passed over the problem of the stability of collagenase and its compatibility with the technology of producing cosmetic substances. According to the authors' data, the enzyme must be stored at a temperature of −20-0° C. At this temperature, the shelf life is three years. Unfortunately, we do not have information on the conditions of the preparation of the test samples of cream formulae used by the authors in the experiment, nor do we have information on whether the end activity of the enzyme was verified in the test samples in the process of its conduct, and under which conditions these samples were stored. However, on the basis of the research of [6] it can be confirmed that the collagenolytic activity of the enzyme is preserved when a cosmetic preparation that contains 0.05% of a specially purified collagenase taken from the livers of king crabs, sea buckthorn or fir oil, extract of propolis and polyethylene oxide gel (as a foundation) is stored at a temperature of +7° C. over the course of six months. In addition to that, at a temperature of +37° C., the activity of the preparation falls to practically zero value over the course of a couple of days. Thus, this is a case in which the storage of a cosmetic substance requires low temperatures.

The pathways of skin aging connected with the modification of other biopolymers. A substantial role is played in the structure and functions of the skin by mucopolysaccharides (glycosaminoglycans), to which group hyaluronic acid belongs. It is found in the granular and lower layers of the epidermis, as well as in the papillary layer of the dermis. The molecular mass of hyaluronic acid may exceed 100 million Da. The repeating fragment of this biopolymer is the bond between glucuronic acid and aminosugar, in which one of the hydrogen atoms of the amino group is located on the acyl fragment (the remainder of acetic acid). Hyaluronic acid has the excellent physical property of being able to create a stable high-viscosity gel with water molecules. This circumstance determines the functions of hyaluronic acid connected with the moisture content of the epidermis and the internal skin structure, as well as its role in the capacity of a cementing substance that binds cells, collagenous bundles, and fibrils together. Like any biopolymer, hyaluronic acid has specific relationships with its corresponding enzyme, hyaluronidase. It is completely clear that this substrate/ferment (hyaluronic acid/hyaluronidase) pair, like collagen and collagenase, participates in the dynamic equilibrium process whose main role is to prevent the collection of hyaluronic acid in the intra- and intracellular bonds in a molecule. The speed of the reaction of the synthesis and destruction of hyaluronic acid, which, apparently, depends on the age of the organism and other parameters, is characterized by half-stages of from 1.9 to 7.7 days, which approximately corresponds to the lifetime of a molecule of hyaluronic acid (from 4 to 16 days). The skin's hyaluronidase largely interacts with hyaluronic acid, which has a high molecular mass; the resulting degradation of hyaluronic acid fragments is conducted by other enzymes. The depolymerization of hyaluronic acid leads to an increase in the skin's permeability and, conversely, a high level of polymerization attainable, among other things, through possible additional cross-links, for example under the influence of products of lipid peroxidation, leading to a decrease in the skin's permeability. This situation is very important, if nothing else because all blood plasma metabolites on the way to basal cells need to pass through the hyaluronic acid gel system, and the speed of their access to the cells depends on the condition of its molecules. Products of cell metabolism are removed from the lymphatic and venous systems in a similar manner. Thus the regulation of the viscosity of the gel made from polysaccharides and water is quite a substantial process. The presence of a barrier to dermal absorption makes pointless the attempts to introduce hyaluronic acid with high molecular masses in cosmetic preparations with the goal of affecting the dynamic equilibrium being examined that is supporting the viscosity of the gel on a certain level. The only attainable result of the introduction of individual hyaluronic acid to cosmetic preparations is the moisturization of the skin's surface. Naturally, we should not exclude effects on the internal structures of the skin of biologically active low-molecular fragments, which may be connected with (included in the gel of) hyaluronic acid. Regarding the low-molecular fragments of hyaluronic acid that are capable of passing through the transepidermal barrier, in analogy with the collagen/collagenase system, we can infer their negative effect due to the hyaluronidase being drawn away from the primary reaction (competitive inhibition). In any case, when we introduce low-molecular substrates of hyaluronic acid, we can expect an increase in the viscosity of the gel formed by the hyaluronic acid, a decrease in the speed of delivery of nourishing substances to the basal cell layer of the epidermis, and an increase in the concentration of products of cellular metabolism in the zones where these cells are located. In accordance with the main postulates of the theory of soft cosmetic influence, the implementation of this kind of event will disrupt the dynamic equilibrium of the formation of the epidermis, speeding up processes leading to skin aging.

Naturally, in an analogy with collagenase, variations on the creation of cosmetic formulae containing hyaluronidase can be examined (see, for example, [7]). The same issues arise here that we attempted to resolve in the previous discussion of the collagen pathway of skin aging:

- the amount of molecular mass of the hyaluronase molecules
- the amount of the optimum concentration of the enzyme
- the stability of the enzyme in the process of the preparation and storage of a cosmetic preparation Basically, collagenase and hyaluronase are important enzymes that require the special attention of cosmetologists. This follows at least from the fact that both enzymes and their substrate pairs (collagen and hyaluronic acid) are localized in the intercellular area of the skin, and the effect of components of cosmetic preparations on the dynamic equilibria of the processes of synthesis and destruction of biopolymers may be directly cooperative in nature. It is a little different, for example, with pairs such as nucleic acids and nucleases. The major events that are associated with the synthesis and destruction of nuclease take place in the intracellular space, separate from the two-layer intercellular lipid membrane. Therefore, only in the case of penetration of the ingredients of cosmetic preparations into the intracellular space is their direct influence possible on the dynamic equilibrium between the gross speed of synthesis and the destruction of nucleic aids, the existence of which out of general considerations, notwithstanding the complexity of the processes being examined, should be in doubt. Otherwise, all options have been implemented connected with either the buildup or deficit of the substrate.

Cosmetic formulae that simultaneously block several mechanisms of skin aging. In concluding the examination of the mechanisms of skin aging, which have been directly or tangentially discussed in various sections of this monograph, a summary should be made. In the aging process of the human body, variations on unfortunate changes may occur that are reflected in the condition of the skin.

A. The processes of lipid peroxidation, the products of which may provoke substantial changes in the function of the skin's cell and biochemical systems.

B. A worsening in the rheological characteristics of the movement of the intercellular fluid that delivers nutrient substances to the basal cells of the epidermis and removes the products of cell metabolism from the area in which these cells are located.

In their turn, the reasons for this worsening may be:

B.1. The narrowing and loss of elasticity of microcapillaries of the circulatory system located in the papillary layer of the dermis.

B.2. The lessening of the permeability of hyaluronic acid gel (and that of other polysaccharides), through which the delivery of nutrient substances and removal of the products of cellular metabolism are conducted.

C. An increase in the inelasticity of the collagen structures in skin.

D. A change to the level and ratio of hormones and hormone-type substances in human blood plasma.

Now on the basis of all of the abovementioned, an ideal cream formula may be presented for the ages of 30-35 and older, for instance. Clearly, it should contain substances that have anti-oxidant activity (blockage of the aging mechanism connected with the implementation of lipid peroxidation [option A]), substances that facilitate an increase in the elasticity of the microcapillaries of the papillary layer of the dermis or other approaches increasing their elasticity (blocking the aging mechanism in relation to option B.1), the hyaluronidase enzyme (blocking the aging mechanism in relation to option B.2), the collagen enzyme (blocking the aging mechanism in relation to option C), and regenerative additives that have activity that is hormonal and regulates cell division (blocking the aging mechanism in relation to option D). For blocking option B.1, the use of a strictly verified concentration of nutrient ingredients dependent on the age of the subject is also possible.

A cosmetic formula for the treatment of cellulite and rejuvenation of the body, which is made of iodized vegetable oils in the form of a vesicle (liposome) and contains thiamucase, hyaluronidase, and other ingredients is known [8]. The use of this formula permits the effective elimination of cellulite, rejuvenation of skin, and removal of scars. The shortcoming of this invention is the formula's lack of ability to adapt to the body of a specific patient, which significantly narrows the effectiveness of the formula in the population (percent effectiveness), the ineffectiveness in the treatment of collagen scars in connection with the lack of collagenase in the formula, the lack of regenerative/anabolic properties in connection with the lack of insulin in the formula, and the applicability of the formula only for cosmetic purposes, which does not provide the opportunity to use the formula in medicine to speed the healing of scar tissue after operative intervention with the purpose of averting commissure disease and the formation of scars.

DISCLOSURE OF THE INVENTION

The task of the invention is the development of a cosmetological and pharmaceutical formula for rejuvenation and restoration of the skin, which has the ability to adapt to the body of a specific person, significantly speed up the postoperative regeneration of tissues, and rejuvenate the skin.

The task set is addressed through the creation of cosmetological and pharmaceutical formulae for the rejuvenation and restoration of skin, including after surgical procedures, containing liposomes with proteins, including an effective quantity of major active ingredients and pharmaceutically acceptable inactive, form-creating ingredients, distinct in that in the capacity of proteins, a supramolecular assembly made of partially acylated proteins is used with a modification level of 0.1 to 10% of the mass of the protein, in which in the capacity of acylated proteins, partially succinated insulin, collagenase, and hyaluronidase may be used alone or in various combinations, and for the creation of the liposomes, phosphatidylcholine and phosphatidylethanolamine may be used in different combinations and obtained by ultrasonication and reverse phase methods. The formula has powerful, regenerative, rejuvenating, and anti-cellulite properties. We used an assembly from a mixture of partially modified proteins (insulin, collagenase, and hyaluronidase), but the molecular charges were partially changed to the opposite. "Assembly" is a term from supramolecular chemistry. The objects of supramolecular chemistry are supramolecular assemblies that self-assemble out of their complements—that is, fragments that have geometrical and chemical correspondence—similar to the self-assembly of the most complex three-dimensional structures in a live cell [9,10]

SHORT DESCRIPTION OF DRAWINGS

FIG. 1. Dependence between Collagen Concentration in the Skin and Age of the Person

EXAMPLES OF INVENTION IMPLEMENTATION

Example 1

Obtaining the formula. 50 ml each of 3% solutions of hyaluronidase, collagenase, and insulin are prepared; they are mixed for the creation of 150 ml of solution with a 1% protein concentration; 105 mg of dry succinic anhydride is added and mixed until fully dissolved. 0.06 g of benzalkonium chloride is added to the solution obtained in the capacity of a preservative. The solution obtained is poured into 10.0 g of a mixture of dry lyophilized phosphatidylcholine liposomes; this is mixed until homogeneity is achieved. 3.0 g of carboxyethylcellulose is added to the suspension obtained; this is mixed until homogeneity is attained and is left to swell for a day. The cream obtained must be stored in a refrigerator.

Example 2

Patient Z., 26 years of age, came to the surgical ward (case history No. 2243) with complaints of gnawing pain in the mesogastrium, nausea, and one instance of vomiting. A worsening in condition was noted over the course of two days. From the medical history: has been suffering from peritoneal commissions since 2006 after appendectomy. Relapse 1-2 times per year. Patient had not self-treated.

Objectively upon arrival: moderately grave condition; a keloidal scar is seen in the right iliac section of the abdomen; palpation induces sharp pain over the entire abdomen; locally, symptoms of Kokher's syndrome are positive. No abnormalities in other systems.

Upon arrival: plan radiography of the organs of the peritoneal cavity: Kloiber's symptoms were distinguished.

Ultrasound showed flat viscero-visceral and viscero-parietal commissures in the right iliac region of the abdomen.

Diagnosis: Peritoneal commissures, algesic form. Dynamic intestinal obstruction.

Treatment was prescribed according to the following method: infusion spasmolytic therapy at a volume of 800.0 ml, spasmolytics, purgative enema. On the second day, a formula with liposomal hyaluronase, collagenase, and insulin in the form of a 1% (protein) suspension in carboxymethyl cellulose was used. In the dynamic on the fifth day, the patient noted a significant improvement in wellbeing and a remitting of the algesic syndrome.

Ultrasound revealed a decrease in the number of flat viscero-parietal commissures.

Upon discharge (23.04.04), the patient did not have any complaints. Clinical palpation indicated that the abdomen was soft and pain-free. Symptoms of abdominal irritation were not present.

Example 3

Patient M., 40 years old, came to the surgical ward (case history No. 3476) with complaints of dull pains in the mesogastrium and of nausea. A worsening in condition was noted over the course of 12 hours. From the medical history: has been suffering from peritoneal commissures since 1993 after a perforated duodenal ulcer occurred. More than one operation on peritoneal commissures (1999, 2001, 2005). Relapse 2-3 times per year.

Objectively upon arrival: moderately grave condition; a keloidal scar is seen in the midline of the abdomen; palpation induces sharp pain over the entire abdomen; locally, symptoms of peritoneal commissure are positive. No abnormalities in other systems.

Upon arrival: plan radiography of the organs of the peritoneal cavity: Kloiber's symptoms were distinguished. The passage of barium through the intestine was slowed and partially permeable.

Ultrasound showed a large quantity of flat viscero-visceral and viscero-parietal commissures in the region of the post-operative scar to the midline of the stomach.

Diagnosis: Peritoneal commissures, algesic form. Partial commissural intestinal blockage.

Treatment was prescribed according to the following method: infusion spasmolytic therapy at a volume of 800.0 ml, spasmolytics, purgative enema. On the second day, a formula with liposomal hyaluronase, collagenase, and insulin in the form of a 1% (protein) suspension in carboxymethyl cellulose was used. In the dynamic on the sixth day, the patient noted an improvement in wellbeing and a remitting of the algesic syndrome. Ultrasound revealed a decrease in the number of flat viscero-parietal commissures. Visually significant scar reduction. The patient underwent an operation: 06.05.08 laparoscopic adhesiolysis. During the operation, a softening of the commissural process was noted, as was the transition of flat commissures into corded or threadlike form.

Upon discharge, the patient did not have any complaints. Clinical palpation indicated that the abdomen was soft and pain-free. Symptoms of abdominal irritation were not present.

Thus the use of a formula of liposomal acylated collagenases, hyaluronizades, and insulin facilitated the remitting of symptoms of commissural intestinal obstructions through regressing commissures of the abdominal cavity.

Industrial Applicability

This invention is related to pharmacology and cosmetology and may be used in the capacity of a medicinal and cosmetic substance for skin anti-aging, scar reduction, treatment of post-operative peritoneal commissures, increasing the speed of post-operative tissue regeneration, and for the liquidation of cellulite. The formula, in the form of a rejuvenating cosmetic cream, may be produced industrially in sufficient quantities, due to the accessibility of all of the formula's components. Unique equipment, high expenditures of energy, and original, difficult-to-access reagents are not necessary for the production of this formula.

References

1 Verzar F., The aging of collagen. Sci.Am., 1963, 208, 104-114;
2 Abdul Malak N., Perrier E. "TIMP-1 like; a new strategy for anti-aging cosmetic formulations" XX Congr. Intern. Federation of the Societies of cosmetic Chemists", Cannes, Sep. 14-18, 1998, V.1, 79-90;
3 "Skin: Structure, function, general pathology, and therapy", eds. A. M. Chernukha, E. P. Frolova. Moscow: Medicine, 1982
4 Hamlin C. R., Kohn R. R., Expl. Gerontol., 7, 377-379 (1972);
5 Sandakhchiev L S, Zinoviyev V V, Tsareva A A et al. "The application of collase for culturing cells", Vopr. Virusol., 39(6)284-286 (1994);
6 Zinoviyev V V, Popova S R et al. "A Substance for Skin Care" Russian Patent No 2089177, 1997;
7 Detsina A N. "A Cosmetic Super-Cream for Skin Care" Russian Patent No 2139039, 1999.
8 U.S. Pat. No. 4,187,291 "Cosmetic composition for the skin"
9 http://dic.academic.ru/dic.nsf/ruwiki/79240
10 Jean-Marie Lehn. Supramolecular Chemistry. Concepts and Perspectives.—Weinheim; New York; Basel; Cambridge; Tokyo: VCH Verlagsgesellschaft mbH, 1995.-P. 103 (Chapter 7)

The invention claimed is:

1. A Cosmetic and pharmaceutical composition comprising liposomes with proteins, wherein the proteins are partially acylated at a modification level of 0.1 to 10% of their mass and are present in the form of a supramolecular assembly, wherein the partially acylated proteins are derived from at least one of collagenase, hyaluronidase, insulin and mixtures thereof.

2. The composition according to claim 1, wherein the partially acylated proteins are derived from hyaluronidase.

3. The composition according to claim 1, wherein the partially acylated proteins are derived from collagenase.

4. The composition according to claim 1, wherein the partially acylated proteins are derived from insulin.

5. The composition according to claim 1, wherein the partially acylated proteins are derived from a mixture of collagenase, hyaluronidase, and insulin.

6. The composition according to claims 1, wherein the partially acylated proteins are produced via reaction of succinic anhydride and proteins.

7. The composition according to claim 1, wherein the liposomes are obtained by a reverse phase method, followed by an ultrasound processing of the liposomes.

8. The composition according to claim 1, wherein the liposomes are obtained by a freeze-thawing method.

9. The composition according to claim 1, wherein the liposomes are obtained by a method of introducing the protein solution to a suspension of lyophilized liposomes.

10. The composition according to claim 1, wherein the liposomes are derived from phosphatidylcholine.

11. The composition according to claim 1, wherein the liposomes are derived from phosphatidylethanolamine.

12. The composition according to claim 1, wherein the liposomes are derived from a mixture of phosphatidylcholine and phosphatidylethanolamine.

13. A method of making the cosmetic and pharmaceutical composition of claim 1, comprising the partial acylation of proteins with a modification level of 0.1 to 10% of their mass and are present in the form of a supramolecular assembly, and incorporating the partially acylated proteins into liposomes, wherein the partially acylated proteins are derived from at least one of collagenase, hyaluronidase, insulin and mixtures thereof.

14. The method according to claim 13, wherein the partially acylated proteins are derived from hyaluronidase.

15. The method according to claim 13, wherein the partially acylated proteins are derived from collagenase.

16. The method according to claim 13, wherein the partially acylated proteins are derived from insulin.

17. The method according to claim 13, wherein the partially acylated proteins are derived from a mixture of collagenase, hyaluronidase and insulin.

18. The method according to claim 13, wherein the partially acylated proteins are produced via a reaction with succinic anhydride.

19. The method according to claim 13, wherein the liposomes are obtained by a reverse phase method, followed by an ultrasound treatment of the liposomes.

20. The method according to claim 13, wherein the liposomes are obtained by freezing-thawing.

21. The method according to claim 13, wherein the liposomes are obtained by introducing a protein solution into a suspension of lyophilized liposomes.

22. The method according to claims 13, wherein the liposomes are derived from phosphatidylcholine.

23. The method according to claim 13, wherein the liposomes are derived from phosphatidylethanolamine.

24. The method according to claim 13, wherein the liposomes are derived from a mixture of phosphatidylcholine and phosphatidylethanolamine.

* * * * *